US006436936B1

(12) United States Patent
Young et al.

(10) Patent No.: US 6,436,936 B1
(45) Date of Patent: *Aug. 20, 2002

(54) METHODS AND COMPOSITIONS FOR TREATING DISORDERS, USING OPTICALLY PURE (+) ZOPICLONE

(75) Inventors: James W. Young, Palo Alto, CA (US); Steven Brandt, Marlborough, MA (US)

(73) Assignee: Sepracor Inc.

( * ) Notice: Subject to any disclaimer, the term of this patent is extended or adjusted under 35 U.S.C. 154(b) by 0 days.

This patent is subject to a terminal disclaimer.

(21) Appl. No.: 09/121,029

(22) Filed: Jul. 22, 1998

Related U.S. Application Data

(63) Continuation of application No. 08/283,497, filed on Aug. 4, 1994, now Pat. No. 5,786,357, which is a continuation of application No. 07/984,039, filed on Dec. 1, 1992, now abandoned, which is a continuation-in-part of application No. 07/801,312, filed on Dec. 2, 1991, now abandoned.

(51) Int. Cl.[7] .................. A61K 31/495; A61K 31/50
(52) U.S. Cl. ..................................... 514/249
(58) Field of Search ........................... 514/249

(56) References Cited

U.S. PATENT DOCUMENTS

| | | | |
|---|---|---|---|
| 3,862,149 A | 1/1975 | Cotrel et al. | 260/268 |
| 4,220,646 A | 9/1980 | Cotrel et al. | 424/250 |
| 4,868,214 A | 9/1989 | Sunshine et al. | 514/568 |
| 4,962,124 A | 10/1990 | Sunshine et al. | 514/568 |
| 5,102,890 A | 4/1992 | Bourz et al. | 514/299 |
| 5,331,000 A | 7/1994 | Young et al. | 514/570 |

FOREIGN PATENT DOCUMENTS

WO    WO 92/12980    8/1992

OTHER PUBLICATIONS

CA 116:75574, Fernandez et al. 1991.*
Fernandez, C. and Baune, B., "Determination of Zopiclone Enantiomers in Plasma by liquid Chromatography Using a Chiral Carbamate Column", J. of Chromatography 572:195–202 (1991).
Bertolasi, V. et al., "Stereochemistry of Benzodiazepine Receptor Ligands. Possible Role of C–H . . . X Interactions in Drug–Receptor Binding and Crystal Structures of CL 218–872, Zopiclone and DMCM", J. Chem. Soc. Perkin. Trans. 2:283–289 (1990).
Jamali, F. et al., "Enantioselective Aspects of Drug Action and Disposition: Therapeutic Pitfalls", J. Pharmaceut. Sci. 78(9):695–715 (1989).
Verma, A. and Snyder, S.H., "Peripheral Type Benzodiazepine Receptors", Annu. Rev. Pharmacol. Toxicol. 29:307–322 (1988).
Brun, J.P., "Zopiclone, a Cyclopyrrolone Hypnotic: Review of Properties", Pharmacology, Biochem. and Behav. 29:831–832 (1988).
Robertson et al., 1988, "Absolute Configuration and Pharmacologic Activities of the Optical Isomers of Fluoxetine, a Selective Serotonin–Uptake Inhibitor", J. Med. Chem. 31(7):1412–1417 (1988).
Jamali, "Pharmacokinetics of Enantiomers of Chiral Non–Steroidal Anti–Inflammatory Drugs", Metab. Pharmacokin. 13(1):1–9 (1988).
Borea, P.A. et al., "Stereochemical Features Controlling Binding and Intrinsic Activity Properties of Benzodiazepine–Receptor Ligands", Molec. Pharmacol. 31:334–344 (1987).
Goa, K.L. and Heel, R.C., "Zopiclone, a Review of Its Pharmacodynamic and Pharmacokinetic Properties and Therapeutic Efficacy as an Hypnotic", Drugs 32(1):48–65 (1986).
Kusnierczyk et al., "Antitumor Activity of Optical Isomers of Cyclophosphamide, Ifosfamide and Trofosfamide as Compared to Clinically Used Racemates", J. immunol. Pharm. 8(4):455–480 (1986).
Jacqmin, P. and Lense, M., "Les Benzodiazepines: Aspects Pharmacodynamiques", J. Pharm. Belg. 40(1):35–54 (1985).
Julou, L. et al., "Pharmacological and Clinical Studies of Cyclopyrrolones: Zopiclone and Suriclone", Pharmacology, Biochem. and Behavior 23:653–659 (1985).

* cited by examiner

Primary Examiner—Russell Travers
Assistant Examiner—Shengjun Wang
(74) Attorney, Agent, or Firm—Sughrue Mion, PLLC

(57) ABSTRACT

Methods and compositions are disclosed utilizing the optically pure (+) isomer of zopiclone. This compound is a potent drug for the treatment of sleep disorders, such as insomnia, and convulsive disorders, such as epilepsy. Similarly, these novel compositions and methods are useful for the treatment of sleep disorders and convulsive disorders while avoiding the concomitant liability of adverse effects associated with the racemic mixture of zopiclone. The optically pure (+) isomer of zopiclone is also useful for treating disorders that are affected by the binding of agonists to central nervous system or peripheral benzodiazepine receptors. Also described are methods and compositions for treating disorders that are affected by binding of agonists to central nervous system or peripheral benzodiazepine receptors while avoiding the adverse effects associated with the administration of the racemic mixture of zopiclone.

9 Claims, No Drawings

METHODS AND COMPOSITIONS FOR TREATING DISORDERS, USING OPTICALLY PURE (+) ZOPICLONE

This is a continuation of application Ser. No. 08/283,497, filed Aug. 4, 1994, now U.S. Pat. No. 5,786,357, which is a continuation of application Ser. No. 07/984,039, filed Dec. 1, 1992, now abandoned, which is a continuation-in-part of application Ser. No. 07/801,312, filed Dec. 2, 1991, now abandoned.

1. BACKGROUND OF THE INVENTION

This invention relates to novel compositions of matter containing optically pure (+) zopiclone. These compositions possess potent activity in treating sleep disorders such as insomnia. These compositions also possess potent activity in treating sleep disorders while avoiding the usual adverse effects including but not limited to bitter taste in the mouth, drowsiness, tiredness in the morning and headache, which are associated with the administration of the racemic mixture of zopiclone. The novel compositions of this invention also possess potent activity in treating convulsive disorders such as epilepsy. These novel compositions useful in treating convulsive disorders avoid the adverse effects which are associated with the administration of the racemic mixture of zopiclone.

Additionally, these novel compositions of matter containing optically pure (+) zopiclone are useful in treating disorders that are affected by the binding of agonists to central nervous system and peripheral benzodiazepine receptors. Such disorders include but are not limited to anxiety, aggressive behavior, muscle tension, behavioral disorders, depression, schizophrenia, and disorders associated with abnormal plasma hormone levels such as endocrine disorders. These novel compositions of matter are useful in treating disorders that are affected by the binding of agonists to central nervous system and peripheral benzodiazepine receptors while avoiding the adverse effects associated with the administration of the racemic mixture of zopiclone.

Also disclosed are methods for treating the above-described conditions or disorders in a human by administering the (+) isomer of zopiclone to said human. Further disclosed are methods for treating the above-described conditions while avoiding the adverse effects that are associated with the racemic mixture of zopiclone, by administering the (+) isomer of zopiclone to said human.

1.1. Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer was a potent teratogen.

The active compound of this composition and method is an optical isomer of the compound zopiclone, which is described in Goa and Heel, [Drugs, 32:48–65 (1986)] and in U.S. Pat. Nos. 3,862,149 and 4,220,646. The chemical structure of zopiclone is shown below:

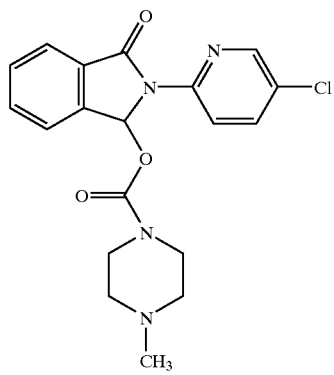

Chemically, this isomer is (+) 6-(5-chloro-pyri-2-dyl)-5-(4-methylpiperazin-1-yl) carbonyloxy-7-oxo-6,7-dihydro-5H-pyrrolo[3-4b]pyrazin or (+) 6-(5-chloro-2-pyridinyl)-6,7-dihydro-7-oxo-5H-pyrrolo[3,4b]pyrazin-5-yl 4-methylpiperazine-1-carboxylate. This isomer, which will hereinafter be referred to as (+) zopiclone, includes the optically pure and the substantially optically pure (+) zopiclone isomer.

Zopiclone, which is the subject of the present invention, is available commercially only as the 1:1 racemic mixture. That is, it is available only as a mixture of optical isomers, called enantiomers.

Zopiclone is the first of a chemically distinct class of hypnotic and anxiolytic compounds that offers a psychotherapeutic profile of efficacy and side effects similar to the benzodiazepines. This class of compounds, the cyclopyrrolones, appears to cause less residual sedation and slowing of reaction times than the benzodiazepines, and it offers the promise of an improved therapeutic index over benzodiazepines.

The pharmacology of zopiclone has been shown both preclinically and clinically to be characterized by five distinct elements. It is predominantly a hypnotic-sedative, offering significant activity on first treatment in the absence of respiratory or cardiac depression. Additionally, zopiclone is an anticonvulsant, and it further exhibits muscle relaxant, anti-aggressive, and anxiolytic activities.

The compound binds to the benzodiazepine receptor complex, or to a site linked closely to this receptor complex. (See Goa, K. L. and Heel, R. C. *Drugs,* 32:48–65, (1986); Brun, J. P., *Pharmacology, Biochemistry and Behavior,* 29:831–832, (1988); Julou, L. et al., *Pharmacology, Biochemistry and Behavior,* 23:653–659, (1985); Verma, A. and Snyder S. H., *Annu. Rev. Pharmacol. Toxicol,* 29:307–322, (1989). The central benzodiazepine receptor is a macromolecular complex that includes a site for the binding of gamma-aminobutyric acid (GABA), the inhibitory neurotransmitter, suggesting that benzodiazepines and chemically unrelated agonists including zopiclone may exert their effects by facilitating the synaptic effects of GABA. While it interacts with the benzodiazepine receptor, zopiclone apparently has minimal effects on memory, no interaction with alcohol, and little or no abuse or dependence potential.

The pharmacologic activity of zopiclone is predominantly that of a sedative or hypnotic, particularly at low doses. Accordingly, the drug may improve sleep in adults and geriatric patients with several types of sleep disorders, and situational, transient primary and secondary insomnia. Following a bedtime dose of zopiclone, there is minimal impairment of psychomotor skills and mental acuity the following morning. The drug is well absorbed from the stomach, and it is not highly bound to plasma proteins.

The racemic mixture of zopiclone is therefore presently used primarily as an hypnotic, improving sleep patterns in chronic insomniacs and providing sleep induction before surgical procedures in hospitalized patients.

Insomnia is characterized by difficulty in sleeping or disturbed sleep patterns. Insomnia may be of a primary nature with little apparent relationship to immediate somatic or psychic events, or secondary to some acquired pain, anxiety or depression. Where possible, treatment is directed to the underlying cause of the condition; hypnotic medication such as zopiclone is generally reserved for insomnia of emotional disturbances and for refractory cases due to more common causes. In these cases, zopiclone provides sedative-hypnotic effects from the first day of treatment, an activity that is maintained following subsequent doses over long treatment periods. There appears to be no diminution or potentiation of activity in adult or geriatric patients, and little or no effect on alertness and performance some ten hours following the bedtime dose. (Brun, J. P., *Pharmacology, Biochemistry and Behavior,* 29:8:31–832, (1988).

In addition, the racemic mixture of zopiclone may be useful in treating other disorders such as convulsive states like epilepsy. Seizure disorder or epilepsy represents a broad group of central nervous system disorders of function that are characterized by recurrent, sudden, often brief attacks, which may alter consciousness, motor activity, sensory phenomena, and autonomic responses, and which may prompt inappropriate behavior. Recurrent seizure patterns of either an idiopathic or symptomatic etiology are termed epilepsy. The most common form of these recurrent but transient episodes are convulsive seizures, which may include loss of consciousness, motor function and control, and which may produce tonic or clonic jerking of the extremities. Pharmacological treatment of epilepsy has been directed to control based on seizure type, rather than etiology. Accordingly, the convulsions have been grouped in broad but rather distinct types including Tonic-clonic (Grand Mal), Partial (Focal) seizures, psychomotor (Complex partial) seizures, pyknoepileptic or Absence (Petit Mal) and the less frequent Myoclonic seizures.

The binding of zopiclone at or near the benzodiazepine receptor complex suggests that the compound may facilitate the inhibitory action of the neurotransmitter GABA and therefore its synaptic effects. As stated above, benzodiazepine receptors, which can be located both within the central nervous system and peripherally (e.g., in the endocrine system), are comprised of macromolecular complexes characterized by sites for binding of the benzodiazepines, GABA, and zopiclone. The benzodiazepine receptor complex is further associated with, and interacts with, a transmembrane channel for chloride ion transport. The effect of zopiclone's interaction with the benzodiazepine receptor/GABA receptor/chloride channel complex is to cause GABA to inhibit cerebral neuronal discharge, presumably by increasing membrane conductance of chloride ion, thus stabilizing membrane potentials and dampening excitatory input. (See Meldrum, B. S., *Brit. J. Clin. Pharm.,* 27 (suppl. 1): 3S–11S, (1989)). It is believed that through mediation of this process zopiclone may be useful in treating epilepsy and a number of other conditions in which GABA is believed to exert a physiologic role. These conditions include anxiety, aggressive behavior, muscle tension, behavioral disorders, depression, schizophrenia, and endocrine disorders.

In addition, the racemic mixture of zopiclone may also be useful to treat anxiety disorder, which can have its etiology in both psychologic and physiologic factors. Emotional stress can precipitate anxiety neurosis which represents the individual's fear of losing control of such emotional drives as aggressive or dependency needs, and losing control of his resulting actions. Physiologically, anxiety is associated with autonomic nervous system discharge and the related neurohumoral processes. In acute anxiety attacks, lasting from a few minutes to an hour, the individual experiences a subjective sense of terror, for no evident reason, and perhaps a haunting dread of catastrophe. Chronic anxiety displays less intense symptoms of longer duration, characterized by uneasiness, nervousness, nagging uncertainty about future events, headache, fatigue, and subacute autonomic symptoms.

Furthermore, the racemic mixture of zopiclone may be useful in treating schizophrenic disorders. Schizophrenic disorders are complex mental disorders which tend toward chronicity, which impair functioning, and which are characterized by psychotic symptoms of disturbed thinking, feeling and general behavior. Clear, goal-directed thought becomes difficult, while blunting and inappropriate affect are the most characteristic emotional changes. Auditory hallucinations can be common, and delusions of persecution are frequent, as are threats of violence, minor aggressive outbursts and aggressive behavior. Disturbances of movement can range from significant overactivity and excitement to retardation and stupor. Treatment has often included tranquilizers with the pharmacologic profile of zopiclone, and other antipsychotic drugs, either orally or by long-acting depot injection to offset problems of patient compliance.

The racemic mixture of zopiclone may also be useful in the treatment of spasticity and acute muscle spasm. Spasticity represents not a single disorder, but rather a range of abnormalities of regulation of skeletal muscle that result from problems at various levels of the central nervous system. A predominant component is heightened muscle tone or hyper-excitability of tonic stretch muscle reflexes. While the pathophysiology of these disorders remains rather poorly understood, it often includes dysfunction of the descending spinal pathways. Presynaptic inhibition of motorneurons, as may be induced by GABA, or agents that in some respects resemble and/or exhibit the pharmacology of GABA, provides some antispastic affect. Additionally, benzodiazepines, or drugs like zopiclone that bind as agonists to the benzodiazepine receptor, may enhance the efficiency of inhibitory GABA-ergic transmission, and thus may provide some efficacy in the treatment or conditions of spasticity, particularly those due to spinal cord lesions.

Acute muscle spasm may be associated with a variety of conditions including trauma, inflammation, anxiety, and pain. While a number of interneuronal blocking agents have been suggested for acute muscle spasm, benzodiazepines and general sedative agents offer comparable efficacy, and therefore prompt the use of racemic zopiclone in the treatment of these conditions.

While the racemic mixture of zopiclone may be useful in the treatment of the above-described disorders, it has a low therapeutic index and also causes adverse effects. These adverse effects include, but are not limited to, the development of a bitter taste due to the salivary secretion of the drug, dry mouth, drowsiness, morning tiredness, headache, dizziness, impairment of psychomotor skills and related effects.

Thus, it would be particularly desirable to find a compound with the advantages of the racemic mixture of zopiclone which would not have the aforementioned disadvantages.

2. SUMMARY OF THE INVENTION

It has now been discovered that the optically pure (+) isomer of zopiclone is useful in treating sleep disorders. It has also been discovered that the use of optically pure (+) zopiclone has a higher potency with respect to therapeutic utility per unit mass than does the racemic mixture of zopiclone. Further, it has been discovered that the optically pure (+) isomer of zopiclone is useful in treating sleep disorders while avoiding adverse effects including but not limited to bitter taste, dry mouth, morning tiredness, headache, dizziness, impairment of psychomotor skills and drowsiness, which are associated with the administration of the racemic mixture of zopiclone.

Also, it has been discovered that these novel compositions of matter containing optically pure (+) zopiclone are useful in treating convulsive disorders such as epilepsy by reason of their higher potency relative to that of racemic zopiclone. In addition, these novel compositions of matter are useful in treating convulsive disorders while avoiding the adverse effects associated with the racemic mixture of zopiclone.

Additionally, these novel compositions of matter containing optically pure (+) zopiclone are useful in treating disorders that are affected by the binding of agonists to central nervous system benzodiazepine receptors including but not limited to anxiety, aggressive behavior, muscle spasms or tension, behavioral disorders, depression and schizophrenia. Furthermore, these novel compositions of matter containing optically pure (+) zopiclone are useful in treating disorders that are affected by the binding of agonists to peripheral benzodiazepine receptors including but not limited to disorders associated with abnormal plasma hormone levels. Representative endocrine disorders that are associated with abnormal release and/or plasma levels of hormones include growth hormone deficiency, gonadotropin deficiency, Cushing's syndrome, Grave's disease, hypothyroidism, and Addison's disease.

In addition, these novel compositions of matter are useful in treating disorders that are affected by the binding of agonists to central nervous system and peripheral benzodiazepine receptors while avoiding the above-described adverse effects associated with the administration of the racemic mixture of zopiclone.

The present invention also includes methods for treating the above-described conditions or disorders in a human by administering the optically pure (+) isomer to said human. In addition, the present invention also includes methods for treating the above described conditions or disorders in a human while avoiding the adverse effects that are associated with the racemic mixture of zopiclone, by administering the optically pure (+) isomer of zopiclone to said human.

3. DETAILED DESCRIPTION OF THE INVENTION

The present invention encompasses a method of treating sleep disorders in a human which comprises administering to a human in need of treatment of said sleep disorder, an amount of (+) zopiclone or a pharmaceutically acceptable salt thereof, substantially free of its (−) stereoisomer, said amount being sufficient to alleviate said sleep disorder.

The present invention also encompasses a composition for the treatment of sleep disorders in a human which comprises an amount of (+) zopiclone or a pharmaceutically acceptable salt thereof, substantially free of its (−) stereoisomer, said amount being sufficient to alleviate said sleep disorder.

In addition, the present invention encompasses a method of treating sleep disorders in a human while avoiding the concomitant liability of adverse effects associated with the administration of racemic zopiclone which comprises administering to a human in need of treatment of sleep disorders, an amount of (+) zopiclone or a pharmaceutically acceptable salt thereof, substantially free of its (−) stereoisomer, said amount being sufficient to alleviate said sleep disorders but insufficient to cause said adverse effects which are associated with administration of racemic zopiclone.

The present invention also encompasses a composition for the treatment of sleep disorders in a human, which comprises an amount of (+) zopiclone or a pharmaceutically acceptable salt thereof, substantially free of its (−) stereoisomer, said amount being sufficient to alleviate said sleep disorders but insufficient to cause said adverse effects, of racemic zopiclone.

The present invention further encompasses a method of treating convulsive disorders in a human which comprises administering to a human in need of anti-convulsant therapy, an amount of (+) zopiclone, or a pharmaceutically acceptable salt thereof, substantially free of its (−) stereoisomer, said amount being sufficient to alleviate said convulsive disorder.

Furthermore, the present invention encompasses a composition for the treatment of convulsive disorders in a human, which comprises an amount of (+) zopiclone or a pharmaceutically acceptable salt thereof, substantially free of its (−) stereoisomer, said amount being sufficient to alleviate said convulsive disorder.

In addition, the present invention encompasses a method of treating convulsive disorders in a human, while avoiding the concomitant liability of adverse effects associated with the administration of racemic zopiclone which comprises administering to a human in need of said anti-convulsant therapy, an amount of (+) zopiclone, or a pharmaceutically acceptable salt thereof, substantially free of its (−) stereoisomer, said amount being sufficient to alleviate said condition but insufficient to cause said adverse effects associated with administration of racemic zopiclone.

Further, the present invention encompasses a composition for the treatment of convulsive disorders in a human, which comprises an amount of (+) zopiclone or a pharmaceutically acceptable salt thereof, substantially free of its (−) stereoisomer, said amount being sufficient to alleviate said convulsive disorder but insufficient to cause adverse effects of racemic zopiclone.

A further aspect of the present invention includes methods of treating disorders that are affected by the binding of agonists to central nervous system (CNS) benzodiazepine receptors, which comprises administering to a human in need of treatment of said disorder, an amount of (+) zopiclone, or a pharmaceutically acceptable salt thereof, substantially free of its (−) stereoisomer, said amount being sufficient to alleviate said sleep disorder.

In addition, the present invention encompasses a composition for the treatment of disorders affected by agonist binding at CNS benzodiazepine receptors, which comprises an amount of (+) zopiclone or a pharmaceutically acceptable salt thereof, substantially free of its (−) stereoisomer, said amount being sufficient to alleviate said disorder.

A further aspect of the present invention includes methods of treating disorders that are affected by the binding of agonists to central nervous system (CNS) benzodiazepine receptors, while avoiding the concomitant liability of adverse effects associated with the racemic mixture of zopiclone, which comprises administering to a human in need of treatment of said disorder, an amount of (+) zopiclone, or a pharmaceutically acceptable salt thereof, substantially free of its (−) stereoisomer, said amount being sufficient to alleviate said disorder but insufficient to cause said adverse effects associated with the administration of racemic zopiclone. Disorders related to agonist binding at CNS benzodiazepine receptors in a human include but are not limited to anxiety, aggressive behavior, muscle spasm or tension, behavioral disorders, depression, and schizophrenia.

In addition, the present invention encompasses a composition for the treatment of disorders affected by agonist binding at CNS benzodiazepine receptors, which comprises an amount of (+) zopiclone or a pharmaceutically acceptable salt thereof, substantially free of its (−) stereoisomer, said amount being sufficient to alleviate said disorder but insufficient to cause adverse effects associated with the administration of racemic zopiclone.

A further aspect of the present invention includes methods of treating disorders that are affected by the binding of agonists to peripheral benzodiazepine receptors, which comprises administering to a human in need of treatment of said disorder, an amount of (+) zopiclone, or a pharmaceutically acceptable salt thereof, substantially free of its (−) stereoisomer, said amount being sufficient to alleviate said sleep disorder.

In addition, the present invention encompasses a composition for the treatment of disorders affected by agonist binding at peripheral benzodiazepine receptors, which comprises an amount of (+) zopiclone or a pharmaceutically acceptable salt thereof, substantially free of its (−) stereoisomer, said amount being sufficient to alleviate said sleep disorder.

A further aspect of the present invention includes methods of treating disorders that are affected by the binding of agonists to peripheral benzodiazepine receptors, while avoiding the concomitant liability of adverse effects associated with the racemic mixture of zopiclone, which comprises administering to said human in need of treatment of such disorder, an amount of (+) zopiclone or a pharmaceutically acceptable salt thereof, substantially free of its (−) stereoisomer, said amount being sufficient to alleviate said disorder but insufficient to cause said adverse effects associated with the administration of racemic zopiclone. Disorders related to agonist binding at peripheral benzodiazepine receptors in a human include disorders associated with abnormal plasma hormone levels.

Hormones, the plasma concentrations of which can be affected by the binding of agonists like zopiclone to peripheral benzodiazepine receptors include, but are not limited to, growth hormone, ACTH, prolactin, luteinizing hormone, and other adrenocortical and testicular hormones. Representative endocrine disorders that are associated with abnormal release and/or plasma levels of hormones include but are not limited to growth hormone deficiency, gonadotropin deficiency, Cushing's syndrome, Grave's disease, hypothyroidism, and Addison's disease.

In addition, the present invention encompasses a composition for the treatment of disorders related to agonist binding at peripheral benzodiazepine receptors, which comprises an amount of (+) zopiclone or a pharmaceutically acceptable salt thereof, substantially free of its (−) stereoisomer, said amount being sufficient to alleviate said disorders but insufficient to cause adverse effects of racemic zopiclone.

The available racemic mixture of zopiclone (i.e., a 1:1 racemic mixture of the two enantiomers) causes sedative-hypnotic, anti-convulsant, muscle relaxant, anti-aggressive, and anxiolytic activity, and provides therapy and a reduction of symptoms in a variety of conditions and disorders related to agonist activity at or near CNS or peripheral benzodiazepine (or GABA) receptors; however, this racemic mixture, while offering the expectation of efficacy, causes adverse effects.

It has now been discovered that by using optically pure or substantially optically pure (+) zopiclone yields an increase in the potency of therapeutic effect as compared to that found in the racemic mixture. In addition, utilizing the optically pure isomer of (+) zopiclone results in clearer dose-related definitions of efficacy, diminished adverse effects, and accordingly, an improved therapeutic index. It is, therefore, more desirable to use the (+) isomer of zopiclone.

The term "adverse effects" includes, but is not limited to bitter taste, drowsiness, morning tiredness, headache, dizziness, dry mouth, and impairment of psychomotor skills.

The term "substantially free of its (−) stereoisomer" as used herein means that the composition contains a greater proportion or percentage of the (+) isomer of zopiclone, in relation to the (−) isomer of zopiclone, these percentages being based on the total amount of zopiclone present. In a preferred embodiment the term "substantially free of its (−) isomer" as used herein means that the composition at least 90% by weight of (+) zopiclone, and 10% by weight or less of (−) zopiclone. In the most preferred embodiment the term "substantially free of the (−) stereoisomer" means that the composition contains at least 99% by weight (+) zopiclone, and 1% or less of (−) zopiclone. In another preferred embodiment, the term "substantially free of its (−) stereoisomer" as used herein means that the composition contains 100% by weight of (+) zopiclone again based on the total amount of zopiclone. The terms "substantially optically pure (+) isomer of zopiclone" and "optically pure (+) isomer of zopiclone" are also encompassed by the above-described amounts.

The term "method of treating sleep disorders" as used herein means relief from insomnia, disturbed sleep patterns, or providing sleep induction before surgical procedures or in disturbed or anxious states. The term, "method of treating convulsive disorders" means relief from the symptoms of epilepsy, which include, but are not limited to, altered consciousness, altered motor activity, autonomic responses, inappropriate behavior patterns, seizures including tonic or clonic jerking of extremities, emotional stress, sense of terror, uneasiness, nervousness, headache, fatigue, auditory hallucinations, aggressive outbursts, acute skeletal muscle spasm, and spasticity.

The term "disorders affected by agonist binding to central nervous system benzodiazepine receptors" includes such conditions as anxiety, aggressive behavior, muscle tension, behavioral disorders, depression, and schizophrenia. The symptoms associated with these disorders and which are alleviated include but are not limited to disturbed thinking, inappropriate affect, sadness, dysphoria, grief, despair, mental slowing, emotional stress, sense of terror, uneasiness, nervousness, headache, fatigue, and auditory hallucinations. The term "disorders affected by agonist binding to peripheral benzodiazepine receptors" includes various endocrine system conditions associated with abnormal plasma hormone levels as mentioned above.

The term "benzodiazepine receptor" as used herein includes the benzodiazepine receptor/GABA receptor/chloride channel complex (benzodiazepine receptor complex) and benzodiazepine receptor-agonist binding sites at or near said receptor complex. Both central nervous system ("central") and peripheral benzodiazepine receptors are encompassed by the use of this term.

The (+) isomer of zopiclone may be obtained by resolution of the mixture of enantiomers of zopiclone using conventional means such as formation of diastereomers using acidic, optically active resolving agents; see, for example "Stereochemistry of Carbon Compounds," by E. L. Eliel (McGraw Hill, 1962) and Lochmuller C. H. et al., $J.$ $Chromatogr.,$ 113: (3) 283–302 (1975).

The magnitude of a prophylactic or therapeutic dose of (+) zopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1.5 mg to about 15 mg. Preferably, a daily dose range should be between about 2.5 mg to about 12.5 mg. Most preferably, a daily dose range should be between about 3.5 mg to about 10.0 mg. In managing the patient, the therapy should be initiated at a lower dose, perhaps about 2.5 mg to about 7.5 mg and increased up to about 10 mg or higher depending-on the patient's global response. It is further recommended that children and patients over 65 years, and those with impaired renal or hepatic function, initially receive low doses, and that they be titrated based on global response and blood level. It may be necessary to use dosages outside these ranges in some cases.

The various terms, "said amount being sufficient to alleviate said sleep disorder," "said amount being sufficient to alleviate said convulsive disorder," "said amount being sufficient to alleviate said disorders," wherein said disorders are those affected by binding at CNS benzadiazepine receptors, and "said amount being sufficient to alleviate said disorders," wherein said disorders are those affected by the binding of agonists to peripheral benzodiazepine receptors are encompassed by the above described dosage amounts and dose frequency schedules. Furthermore, the various terms "an amount sufficient to alleviate said sleep disorders but insufficient to cause adverse effects," "an amount sufficient to alleviate said condition but insufficient to cause said adverse effects," wherein said conditions are convulsive disorders such as epilepsy and "an amount sufficient to alleviate said condition but insufficient to cause said adverse effects" wherein said conditions are disorders affected by the binding of agonists to central nervous system and peripheral benzodiazepine receptors are encompassed by the above described dosage amounts and dose frequency schedules.

Any suitable route of administration may be employed for providing the patient with an effective dosage of (+) zopiclone. For example, oral, rectal, parenteral, transdermal, subcutaneous, intramuscular, and the like may be employed. Dosage forms include tablets, troches, dispersions, suspensions, solutions, capsules, patches, and the like.

The pharmaceutical compositions of the present invention comprise (+) zopiclone as active ingredient, or a pharmaceutically acceptable salt thereof, and may also contain a pharmaceutically acceptable carrier, and optionally, other therapeutic ingredients.

The term "pharmaceutically acceptable salts" refers to salts prepared from pharmaceutically acceptable non-toxic acids including but not limited to inorganic acids and organic acids.

Salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids.

The compositions include compositions suitable for oral, rectal and parenteral (including subcutaneous, intramuscular, and intravenous) administration, although the most suitable route in any given case will depend on the nature and severity of the condition being treated. The most preferred route of the present invention is the oral route. The compositions may be conveniently presented in unit dosage form, and prepared by any of the methods well known in the art of pharmacy.

In the case where an oral composition is employed, a suitable dosage range for use is from about 1.5 mg to about 15.0 mg with, in the usual case, the lower doses serving more common insomnia, and the higher doses, presented in divided dosing, reserved for control of psychiatric disorders. Preferably, a dose range of between about 2.5 mg to about 12.5 mg is given as a once daily administration or in divided doses if required; most preferably, a dose range of from about 3.5 mg to about 10 mg is given, either as a once daily administration or in divided doses if required. Patients may be upward titrated from below to within this dose range to a satisfactory control of symptoms as appropriate.

In practical use, (+) zopiclone can be combined as the active ingredient in intimate admixture with a pharmaceutical carrier according to conventional pharmaceutical compounding techniques. The carrier may take a wide variety of forms depending on the form of the preparation desired for administration, e.g., oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as suspensions, solutions, and elixirs); aerosols; or carriers such as starches, sugars, microcrystalline cellulose, diluents, granulating agents, lubricants, binders, disintegrating agents and the like, in the case of oral solid preparations (such as powders, capsules, and tablets) with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, and/or surface active or dispersing agent.

Molded tablets may be made by molding in a suitable machine a mixture of the powdered compound moistened with an inert liquid diluent. Desirably, each scored tablet contains from about 2.5 mg to about 7.5 mg of the active ingredient, and each cachet or capsule contains from about 2.5 mg to about 7.5 mg of the active ingredient, (+) zopiclone. Most preferably, the tablet, cachet or capsule contains either one of three dosages, about 2.5 mg, about 5.0 mg and about 7.5 mg of the active ingredient.

The invention is further defined by reference to the following examples describing in detail the preparation of the compound, and the compositions of the present invention. It will be apparent to those skilled in the art that many modifications, both to materials and methods, may be practiced without departing from the purpose and interest of this invention.

4. EXAMPLES

4.1. Example 1

A pharmacologic study is conducted to determine the relative potency, comparative efficacy, and binding affinity of the enantiomers and racemic mixture of zopiclone.

The pharmacologic profile of hypnotic-sedative, anxiolytic agents of the benzodiazepine class has been rather well established (Goodman and Gilman: *The Pharmacological Basis of Therapeutics*, 7th. Edition, Chapt. 17, 340–351, (1985), MacMillan Publishing Co., N.Y.) and has been extended to non-benzodiazepine agents of the cyclopyrrolone class (Bardone, M. C. et al., Abstract No. 2319, 7th. Int. Congr. Pharm. Paris, July, 1978, Pergamon Press, London; Julou, L. et al., *Pharmacology, Biochemistry and Behavior*, 23:653–659 (1985)).

A variety of experimental models, which are rather well characterized (Julou, L. et al., ibid, 1985) can be used to characterize the various activities of racemic zopiclone and its pure isomers—namely, its anticonvulsant, myorelaxant, anti-aggressive, sedative-hypnotic, and anxiolytic activities. In an examination of each element of the pharmacologic profile, racemic zopiclone and its optically pure stereoisomers are compared and contrasted with such pharmacologic standards as nitrazepam and diazepam, two benzodiazepine agents, in a variety of animal models. The dose (mg/kg) of each agent that is capable of inhibiting by 50% (the $ID_{50}$ or $ED_{50}$) an induced response in rodents, for example, provides the basis for comparison. Thus, pentylenetetrazole-induced convulsions, picrotoxin convulsions, and electrically-induced convulsions can be used to demonstrate the anticonvulsant activity of zopiclone (Haefely, W., *Psychotropic Agents*, eds. Hofmeister, F. and Stille, G., Springer Verlag, Berlin, Part 11, 12–262, (1981)). Further, in the rat, in the amygdala kindled model of epilepsy, daily electrical stimulation of the amygdala induces a progressive increase of epileptic afterdischarge duration, with increasing epileptic behavioral symptoms, producing in some two weeks a generalized convulsive crisis. Presumably, previously ineffective stimuli have sensitized neuronal pathways, and it has been suggested that a similar mechanism may exist for the induction of an anxiety state in man after repeated stresses.

Similar models are available for determination of the myorelaxant, anti-aggressive, and sedative-hypnotic activities of racemic zopiclone and its optically pure enantiomers in both mice and rats. (For review see Julou, L. et al., ibid, 1985.)

The pharmacologic activity of the enantiomers and the racemic mixture of zopiclone may be compared for their affinity for binding to both CNS and peripheral benzodiazepine receptors. In this biochemical affinity binding study, the binding of the $^3H$-radiolabelled enantiomers and racemic mixture of zopiclone are studied in a synaptosomal membrane preparation of cerebral tissue from female rat brain, prepared by homogenization in ice-cold isosmotic (0.32 M) sucrose, and centrifugation, first at low speed (1,000×g for 10 min.), with the resultant supernatant solution then being centrifuged at high speed (48,000×g for 20 min). The resulting pellet is suspended in Kreb-Tris buffer at pH 7.4, and the concentration of protein is adjusted to 15 mg/ml. This synaptosomal membrane preparation may be stored at −18° C. until used at temperatures of 22° C. (room temp.) with the radio-cyclopyrrolone in Kreb-Tris buffer solution pH 7.4. Following a 30-minute incubation, separation of the bound and free drug is performed by centrifugation at 1,000×g for 10 minutes in scintillation vials. The supernatant solution is collected, the pellet is dissolved in a counting vehicle, and the radioactivity is counted in a liquid scintillation counter. The original supernatant solution from the first incubation, which contains unbound radiolabelled drug, may be further used in additional binding studies using the same method. Additional controls involve, for instance, study of the radioactivity bound in the presence of 10 uM flunitrazepam (a benzodiazepine), which experiment is useful in assessing non-specific binding. Furthermore, the binding of various concentrations of the radio-labelled zopiclone isomers and their racemic mixture in the presence of a fixed concentration of GABA provides additional information as to the modulation of the GABA-ergic system by the zopiclone enantiomers. (For review see Jacqmin, P., et al., *Arch. Int. Pharmacodyn*, 282:26–32 (1986); Jacqmin, P., et al., *J. Pharm. Belg.*, 40:35–54 (1985)). As regards the peripheral benzodiazepine receptors and their distinction from central benzodiazepine and zopiclone binding sites, see the review of Verma and Snyder Verma, A. and Snyder, S. H., *Ann. Rev. Pharmacol. Toxicol.*, 29:307–322 (1989) which is hereby incorporated by reference.

The enantiomers and racemate of zopiclone are thus characterized by their relative activities at these receptor binding sites, coupled with their pharmacologic profiles of activity.

The acute toxicity of the enantiomers of zopiclone and of the racemic mixture thereof are determined in studies in which rats are administered progressively higher doses (mg/kg) of the pure isomers or racemate. That lethal dose which, when administered orally, causes death of 50% of the test animals, is reported as the $LD_{50}$. Comparison of LD50 values for the enantiomers and racemate provides a measure of the relative toxicities of the compositions.

4.2. Example 2

Effects on Psychomotor Behavior

Ten parameters are measured (pinna reflex, spontaneous activity, palpebral size, startle response, touch response, reactivity, placing, righting reflex, exploration, and ataxia). Each parameter scores 2 points for normalcy for a total of 20 points×3 mice=60 points possible. Scores below 40 (<40) denote behavioral deprsesion. Scores are determined before and after dosing with test sample. See Irwin, S., *Psychopharrmacologia*, 13:222–257 (1968).

| REFERENCE AGENTS ($ED_{100}$, mg/kg): | |
|---|---|
| chlordiazepoxide | 100 |
| chlorpromazine | 25 |
| clozapine | 25 |
| diazepam | 50 |
| glutethimide | 300 |
| haloperidol | 10 |
| meprobamate | 300 |
| pentobarbital | 100 |
| phenobarbital | 150 |
| reserpine | 50 |
| thioridazine | 50 |

4.3. Example 3

ORAL FORMULATION
Capsules:

| Formula | Quantity per capsule in mg. | | |
|---|---|---|---|
|  | A | B | C |
| Active ingredient (+) zopiclone | 2.5 | 5.0 | 7.5 |
| Lactose | 77.0 | 74.5 | 72.0 |
| Corn Starch | 20.0 | 20.0 | 20.0 |
| Magnesium Stearate | 0.5 | 0.5 | 0.5 |
| Compression Weight | 100.0 | 100.0 | 100.0 |

The active ingredient, (+) zopiclone, lactose, and corn starch are blended until uniform; then the magnesium stearate is blended into the resulting powder. The resulting mixture is encapsulated into suitably sized two-piece hard gelatin capsules.

4.4. Example 4

ORAL FORMULATION
Tablets

| Formula | Quantity per Tablet in mg. | | |
|---|---|---|---|
|  | A | B | C |
| Active ingredient, (+) Zopiclone | 2.5 | 5.0 | 7.5 |
| Lactose BP | 151.0 | 148.5 | 146.0 |
| Starch BP | 30.0 | 30.0 | 30.0 |
| Pregelatinized Maize Starch BP | 15.0 | 15.0 | 15.0 |
| Magnesium Stearate | 1.5 | 1.5 | 1.5 |
| Compression Weight | 200.0 | 200.0 | 200.0 |

The active ingredient, (+) zopiclone, is sieved through a suitable sieve and blended with lactose, starch, and pregelatinized maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

What is claimed is:

1. A method of treatment of symptoms of epilepsy in a human, which comprises administering to a human in need of such treatment, a therapeutically effective amount of zopiclone in the form of (+) zopiclone or a pharmaceutically acceptable salt thereof, wherein the amount of (+) zopiclone or a pharmaceutically acceptable salt thereof, is greater than approximately 90% by weight of the total weight of zopiclone administered.

2. The method of claim 1, wherein (+) zopiclone is administered by intravenous infusion, by transdermal delivery, or orally.

3. The method of claim 1, wherein (+) zopiclone is administered in an amount of from about 1.5 mg to about 15.0 mg per day.

4. The method of claim 3, wherein (+) zopiclone is administered in an amount of from about 2.5 mg to about 12.5 mg per day.

5. The method of claim 4, wherein (+) zopiclone is administered in an amount of from about 3.5 mg to about 10.0 mg per day.

6. The method of claim 1, wherein (+) zopiclone, or a pharmaceutically acceptable salt thereof, is administered together with a pharmaceutically acceptable carrier.

7. The method of claim 1, wherein the amount of (+) zopiclone, or a pharmaceutically acceptable salt thereof, is at least 99% by weight of the total weight of zopiclone administered.

8. The method of claim 1, wherein zopiclone is administered in the form of a substantially optically pure (+) isomer of zopiclone.

9. The method according to claim 2, wherein (+) zopiclone is administered as a tablet or as a capsule.

* * * * *